(12) United States Patent
Enerson (10) Patent No.: US 6,543,745 B1
(45) Date of Patent: Apr. 8, 2003

(54) MALE LUER VALVE

(75) Inventor: Jon R. Enerson, Port Richey, FL (US)

(73) Assignee: Halkey-Roberts Corporation, St. Petersburg, FL (US)

( * ) Notice: Subject to any disclaimer, the term of this patent is extended or adjusted under 35 U.S.C. 154(b) by 0 days.

(21) Appl. No.: 10/261,375

(22) Filed: Oct. 1, 2002

Related U.S. Application Data (60) Provisional application No. 60/327,817, filed on Oct. 9, 2001.

(51) Int. Cl.[7] .......................... A61M 39/26; F16K 21/04
(52) U.S. Cl. ....................................... 251/149.7; 251/86
(58) Field of Search ..................... 251/149.6, 149.7, 251/86

(56) References Cited

U.S. PATENT DOCUMENTS

| | | | | |
|---|---|---|---|---|
| 2,503,495 A | * | 4/1950 | Koester | 251/149.6 |
| 3,199,831 A | * | 8/1965 | Sully | 251/149.6 |
| 4,436,125 A | * | 3/1984 | Blenkush | 251/149.6 |
| 5,429,155 A | * | 7/1995 | Brzyski et al. | 251/149.6 |
| 5,950,986 A | * | 9/1999 | Daugherty et al. | 251/149.6 |
| 6,299,132 B1 | | 10/2001 | Weinheimer | 251/149.6 |

* cited by examiner

Primary Examiner—Paul J. Hirsch
(74) Attorney, Agent, or Firm—Trexler, Bushnell, Giangiorgi, Blackstone and Marr, Ltd.

(57) ABSTRACT

A valve that has at least one internal port on a valve core and at least one an internal slot in a valve body. The valve core is biased into a position wherein the port of the valve core is aligned with a sealing surface of the valve body thereby prohibiting fluid flow through the valve. The valve core is slidable such that the port of the valve core becomes aligned with the internal slot of the valve body thereby allowing fluid flow through the valve. Another valve includes a self-aligning valve seat carrier which is pivotably engaged with a valve core member. The self-aligning valve seat carrier engages a sealing surface in a valve body to prohibit fluid flow through the valve, but the valve core is slidable such that the self-aligning valve seat carrier disengages from the sealing surface in order to allow fluid flow through the valve.

14 Claims, 6 Drawing Sheets

MALE LUER VALVE

BACKGROUND

This invention generally relates to valves such as luer lock valves which are used primarily in the medical field, and more specifically relates to a slidable type of valve used primarily in the medical field.

Slidable valves presently exist for use in the medical field. Such valves provide that the valve is initially biased into a closed position, where fluid cannot flow through the valve, and one or more internal components of the valve are slidable within the valve to actuate the valve into an open position, where fluid can flow through the valve.

Figure 1:
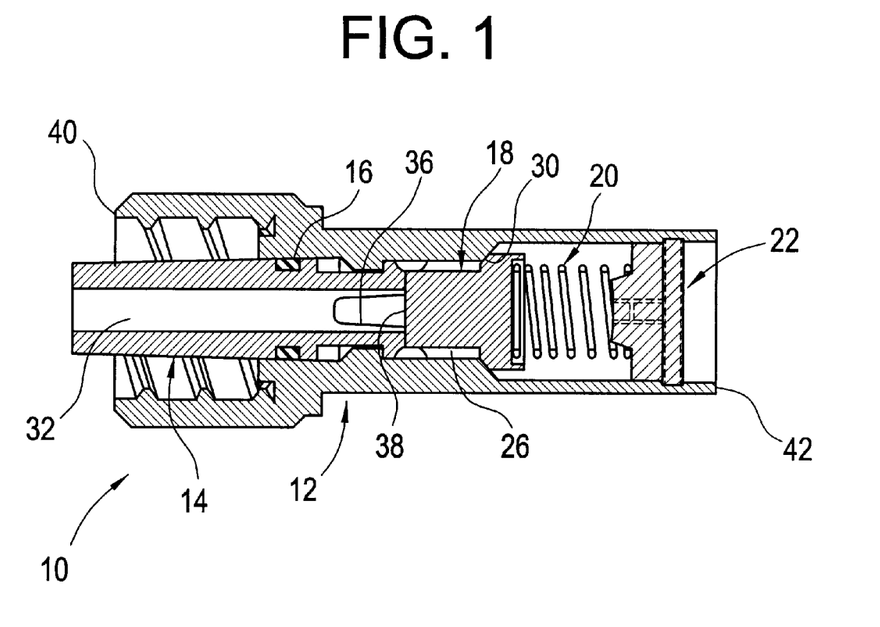
FIG. 1 is a side, cross-sectional view of the valve which is the subject of U.S. patent application Ser. No. 09/523,354, showing the valve in a closed position.
Figure 2:
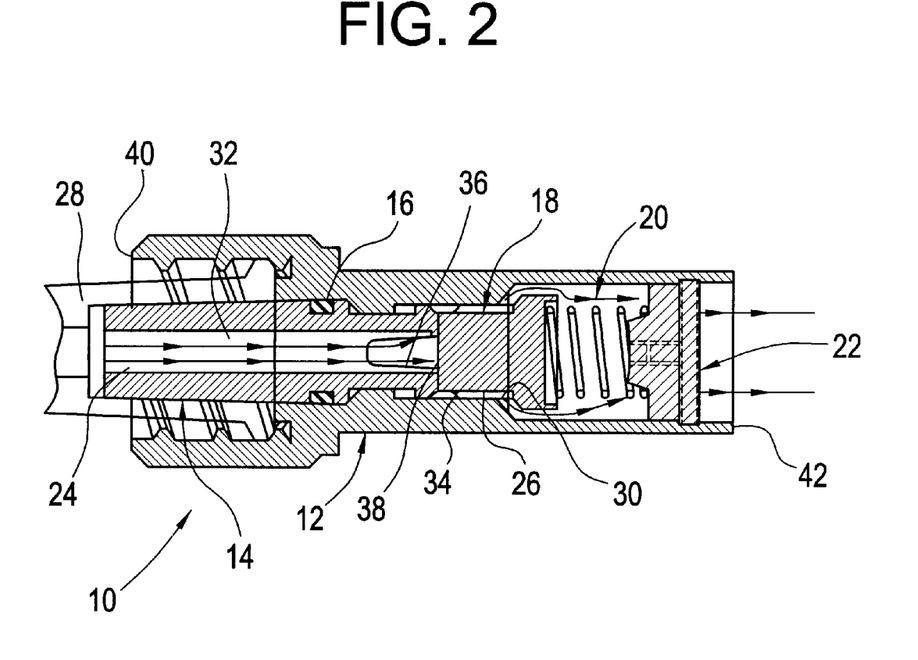
FIG. 2 is a view similar to FIG. 1, but showing the valve in an open position.

One type of medical valve is the subject of United States patent application Ser. No. 09/523,354, now U.S. Pat. No. 6,299,132 and is shown in FIGS. 1 and 2 of the present application. Specifically, FIG. 1 shows the valve 10 in the closed position (wherein fluid cannot flow through the valve), and FIG. 2 shows the valve 10 in the open position (wherein fluid can flow through the valve). The valve 10 includes a valve body 12, a valve poppet 14 with luer taper (with sealing member 16 thereon), an internal resilient valve stem 18, a metal compression spring 20 and a valve plug 22, all of which are within the flow path of fluid moving through the valve (the arrows 24 shown in FIG. 2 illustrate the fluid flow path (in one of two possible directions) through the valve 10). The valve stem 18 may include flutes or ribs on an external surface 26 thereof to facilitate fluid flow around the stem 18 when the valve 10 is in the open position.

In use, engagement or mating structure 28, such as a syringe, another valve or some other structure, engages the valve poppet 14, pushing it generally into the valve body 12 causing the valve 10 to move from the closed position as shown in FIG. 1 to the open position as shown in FIG. 2. As shown in FIG. 2, when the valve 10 is in the open position, the valve stem 18 is disengaged from a valve seat 30 in the valve 10. This provides that fluid can ultimately flow from a bore 32 provided in the valve poppet 14 to an area 34 adjacent the periphery of the valve stem 18, or vice versa if the fluid is flowing in the opposite direction.

In the case where the fluid flows from left-to-right in FIG. 2, fluid initially enters the bore 32 in the valve poppet 14 (i.e. from the mating structure 28), and travels to a notch 36 in the valve poppet 14 (and/or to a notch (not shown) in surface 38 of the valve stem 18). The valve stem 18 deflects the fluid to an area 34 adjacent the periphery of the valve stem 18, and the fluid flows along the external surface 26 of the valve stem 18 (and along the ribs, if provided, on the external surface 26 of the valve stem 18), past the valve seat 30, along the compression spring 20, and out the plug 22, and specifically between fins of the plug 22 and out the valve 10. In the opposite direction, fluid flows into the plug 22 of the valve 10, along the compression spring 20, past the valve seat 30, along the periphery of the valve stem 18 (and along the ribs, if provided, on the external surface 26 of the valve stem 18), to the notch 36 in the valve poppet 14 (and/or to a notch (not shown) in surface 38 of the valve stem 18), and through the bore 32 in the valve poppet 14 to the mating structure 28.

The overall design of the valve shown in FIGS. 1 and 2—being that there are so many components in the fluid flow path—results in substantial restriction to fluid flow through the valve 10. As a result, the valve 10 cannot effectively conduct fluids having viscosities of 1.0 to 1.5 centipoise and above. Additionally, the design provides that there are numerous cavities or "dead areas" for entrapment of fluid within the valve 10. The existence of dead areas, and the fact that there so many components in the fluid flow path, creates turbulence in the fluid flow as the fluid flows through the valve 10. The turbulence renders the valve 10 a poor candidate for transmitting human blood, blood products, or any other material which is sensitive to turbulence. With regard to blood, concerns of lycing (i.e. damage to blood cells) and retention of clotted blood within the valve 10 gives rise to problems with possible infusion of thrombolotics or fibrous re-injection into a patient. The low viscosity conduction limits of the valve design shown in FIGS. 1 and 2 restrict its utilization for high viscosity materials, thus limiting broader employment of the valve in a clinical environment.

Furthermore, the design shown in FIGS. 1 and 2 provides that while the valve poppet 14 is installed through the one end 40 of the valve 10, the other components (i.e. the valve stem 18, compression spring 20, and plug 22) are installed through the other end 42. This complicates and increases the cost of the assembly process.

OBJECTS AND SUMMARY

A general object of an embodiment of the present invention is to provide a valve which has increased flow rate and an unobstructed fluid flow path.

Another object of an embodiment of the present invention is to provide a valve which has fewer components within the fluid flow path.

Still another object of an embodiment of the present invention is to provide a valve which causes less turbulence to the fluid flow.

Still yet another object of an embodiment of the present invention is to provide a valve which minimizes the residual volume (i.e. "dead areas") contributing to fluid entrapment.

Still yet another object of an embodiment of the present invention is to provide a method of assembling a valve wherein components are installed through one end of a valve body, but not the other.

Briefly, and in accordance with at least one of the foregoing objects, an embodiment of the present invention provides a valve that has at least one internal port which aligns with an internal slot to permit fluid flow. Specifically, the valve includes a valve body that has a sealing surface and at least one internal slot. A valve core is disposed in the valve body, and the valve core includes at least one port. Spring means is engaged with the valve body and valve core, and the spring means biases the valve core into a closed position wherein the port of the valve core is aligned with the sealing surface of the valve body thereby prohibiting fluid flow through the valve. The valve core is slidable within the valve body such that the valve is actuated into an open position wherein the port of the valve core becomes aligned with the internal slot of the valve body thereby allowing fluid flow through the valve. Preferably, at least one end of the valve is configured for a luer lock fitting.

A bore extends through the valve core, along a longitudinal axis thereof, and the bore defines a fluid flow area. The one or more ports on the valve core which align with the sealing surface of the valve body when the valve is in the closed position and with the one or more slots in the valve body when the valve is in the open position consists of one or more openings in a wall of the valve core. The valve body also includes a fluid flow area. Hence, a fluid flow path through the valve is defined by the fluid flow area defined through the valve core (i.e. the bore and the one or more ports) and the fluid flow area of the valve body. The spring means is generally between the valve body and valve core, but is not within the fluid flow path through the valve.

Preferably, each slot in the valve body is larger than each respective port of the valve core, and each port of the valve core is larger than a cross-sectional diameter of the bore which extends through the valve core. Preferably, the valve core includes two ports and the valve body includes two corresponding slots which align with each other when the valve core slides within the valve body to the open position. The ports of the valve core and the slots of the valve body are preferably 180 degrees apart relative to each other.

Preferably, a first sealing member and a second sealing member are disposed on the valve core, where the first sealing member engages the sealing surface of the valve body whether the valve core is in the open or the closed position, and the second sealing member engages with the sealing surface of the valve body when the valve core is in the closed position, but disengages from the sealing surface of the valve body when the valve core is in the open position. The valve core may include at least one barb which abuts against an internal surface of the valve body when the valve core is biased into the closed position by the spring means. Preferably, the valve body includes a pocket, the valve core includes a shoulder, and the spring means is disposed in the pocket of the valve body and engages the shoulder of the valve core. Again, preferably the spring means is generally between the valve body and valve core, but is not within the fluid flow path through the valve. As an alternative to the sealing members, a resilient material may be over-molded or co-injected on the valve core to enhance the seal with the structure which is engaged with the valve and to enhance the seal between the valve core and valve body.

Another embodiment of the present invention provides a valve that includes a self-aligning valve seat carrier which is pivotably or adjustably engaged with a valve core member. Specifically, the valve includes a valve body which includes a sealing surface, and the valve core is disposed in the valve body. The self-aligning valve seat carrier also includes a sealing surface. Spring means is engaged with the valve body and the valve core, and the spring means biases the valve core into a closed position wherein the sealing surface of the self-aligning valve seat carrier engages the sealing surface of the valve body thereby prohibiting fluid flow through the valve. The valve core is slidable within the valve body such that the valve is actuated to an open position wherein the sealing surface of the self-aligning valve seat carrier disengages from the sealing surface of the valve body thereby allowing fluid flow through the valve.

The self-aligning valve seat carrier may take several different configurations. For example, the self-aligning valve seat carrier may include a pair of arms which engage corresponding recessed grooves proximate the end of the valve core, may include a ball which engages a corresponding socket on the valve core, or may include a barb which engages corresponding structure on an end of the valve core. A sealing member may be disposed on the valve seat carrier, or a sealing material may be co-injected or over-molded onto the exterior surface thereof.

Another aspect of the present invention provides a method of assembling a valve. The method includes installing a plurality of components through one end of a valve body, and installing no components through an opposite end of the valve body. Hence, the assembly process is simplified and less costly.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DESCRIPTION

While the present invention may be susceptible to embodiment in different forms, there are shown in the drawings, and herein will be described in detail, embodiments thereof with the understanding that the present description is to be considered an exemplification of the principles of the invention and is not intended to limit the invention to that as illustrated and described herein.

Figure 3:
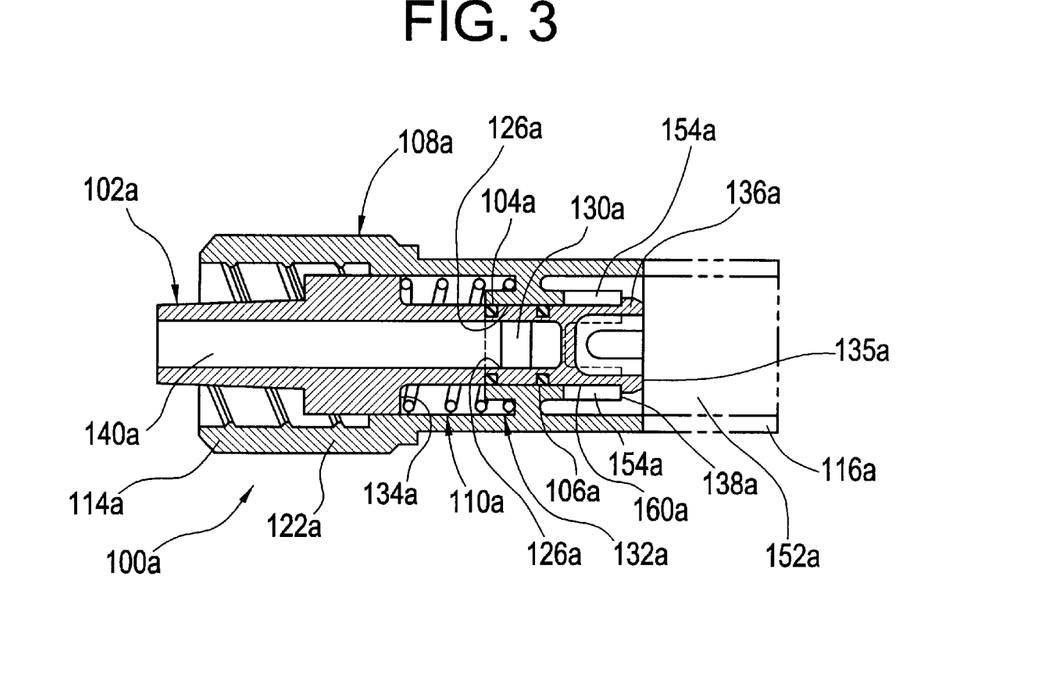
FIG. 3 is a side, cross-sectional view of a valve which is in accordance with an embodiment of the present invention, showing the valve in a closed position.
Figure 4:
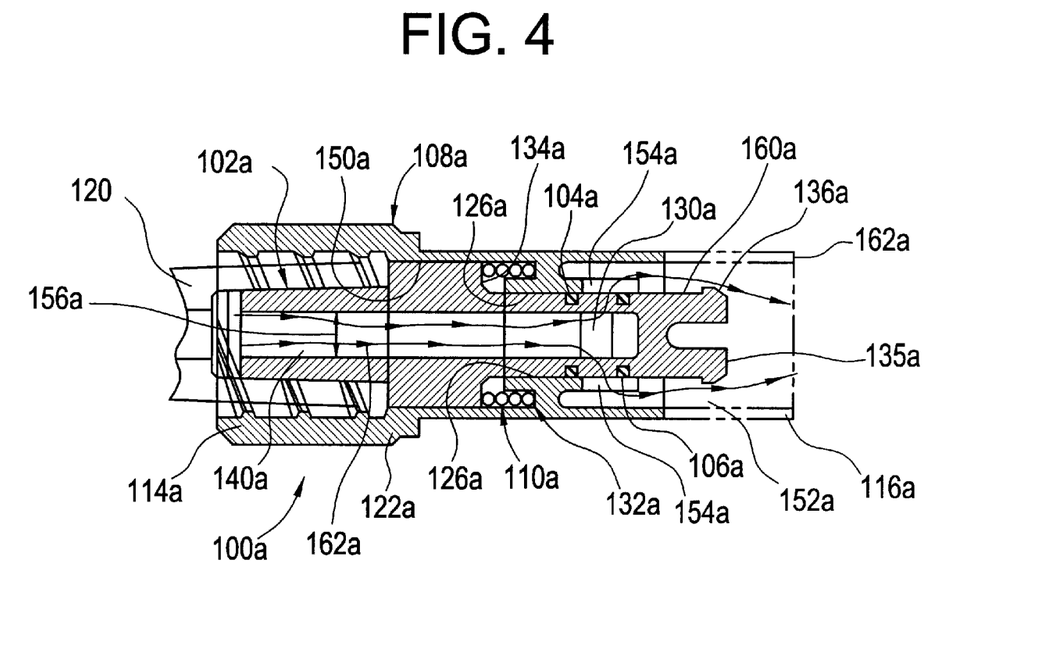
FIG. 4 is a view similar to FIG. 3, but showing the valve in an open position.
Figure 5:
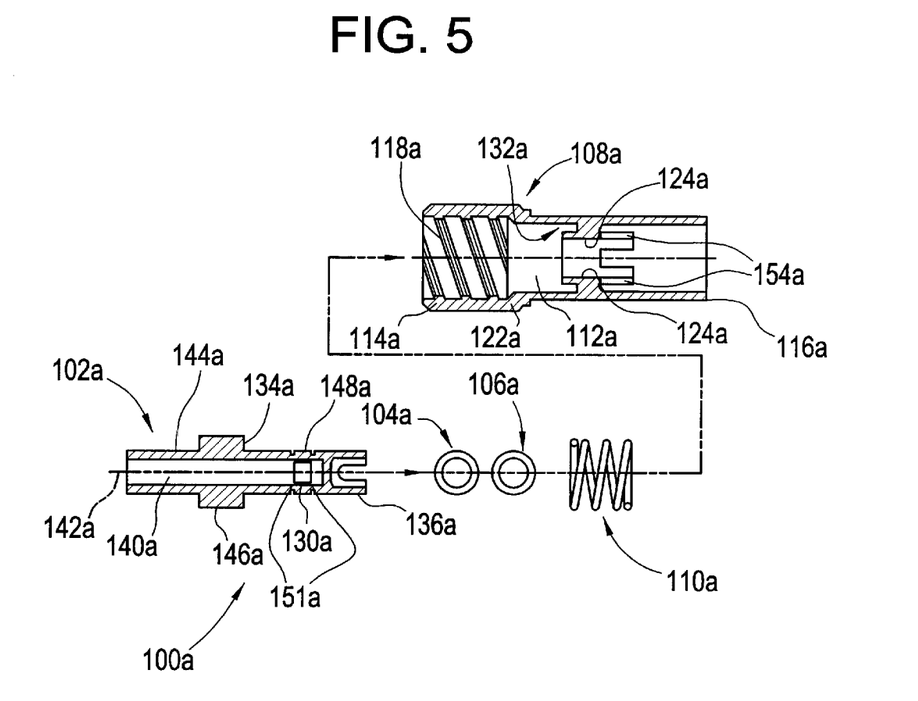
FIG. 5 is an exploded view of the valve shown in FIGS. 3 and 4, illustrating that the valve is assembled from a distal end of the valve body.
Figure 6:
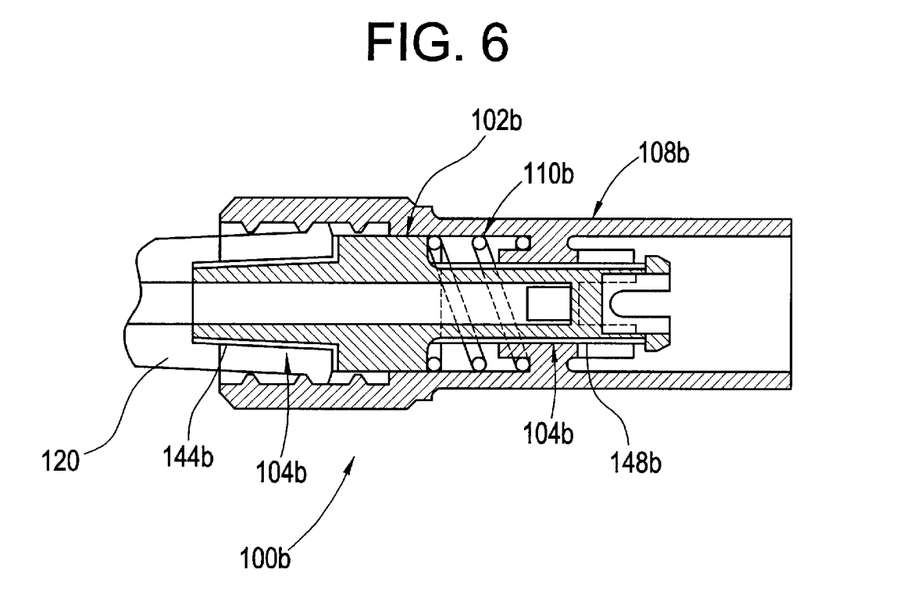
FIG. 6 is a side, cross-sectional view of a valve which is in accordance with an another embodiment of the present invention.
Figure 7:
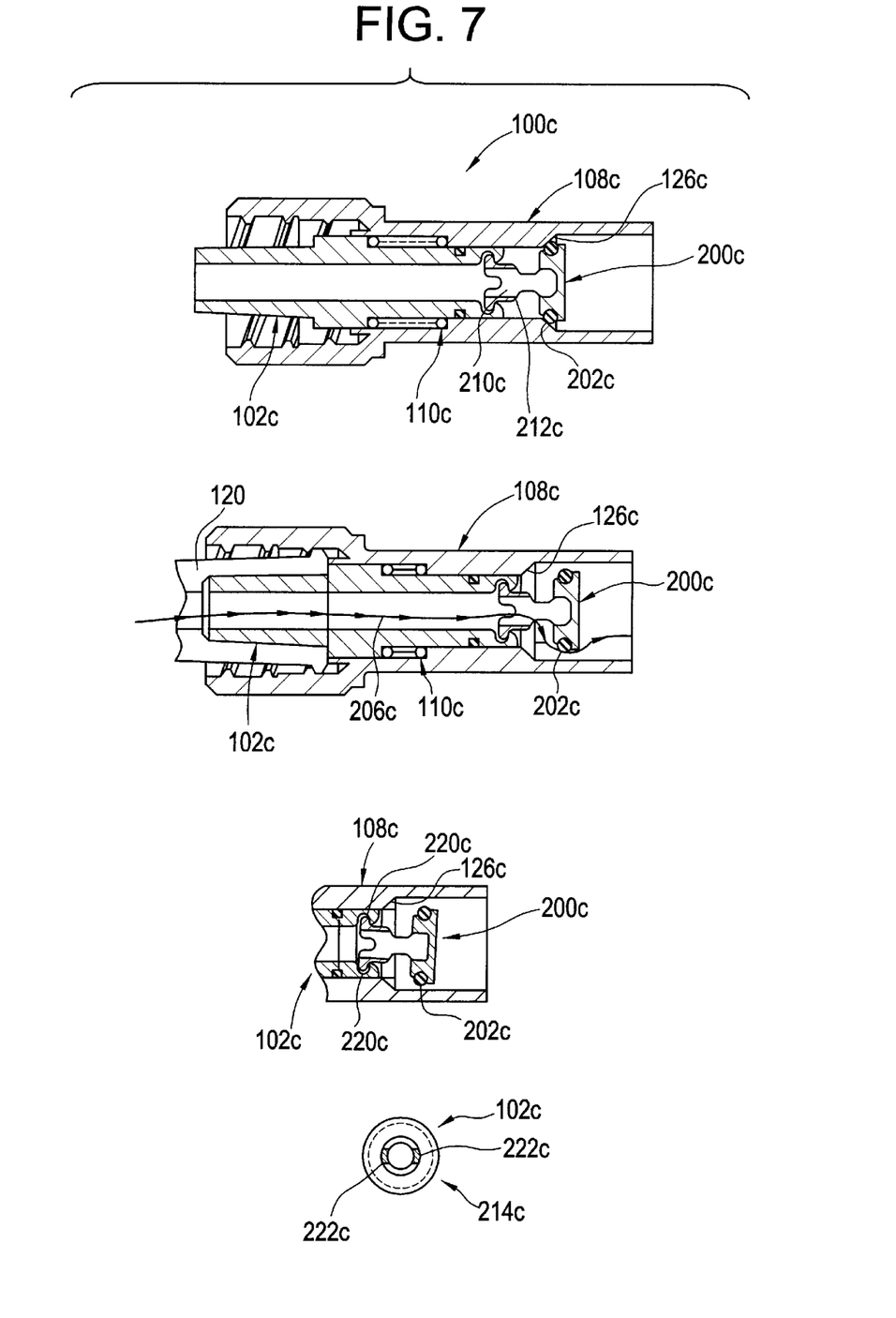
FIG. 7 is a set of views relating to a valve which is in accordance with still yet another embodiment of the present invention, specifically there are three side, cross-sectional views—a top-most partial cross-sectional view showing the valve in the closed position, a middle partial cross-sectional view showing the valve in the open position, and a bottom-most partial cross-sectional view showing pivoting of a self-aligning valve seat carrier of the valve—as well as a plan view of the bottom of a valve core of the valve with the valve seat carrier removed.
Figure 8:
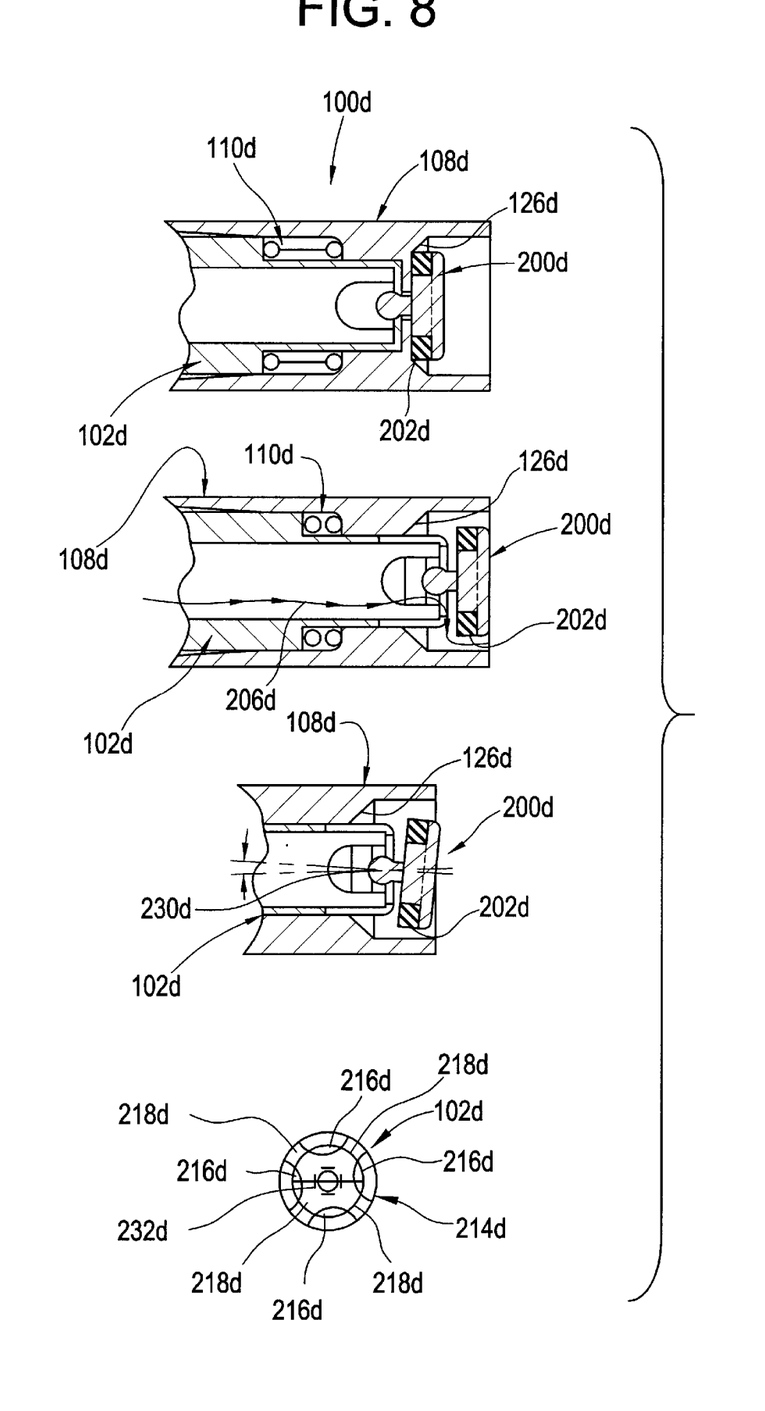
FIG. 8 is a set of views similar to FIG. 7, but relating to a valve which is in accordance with still yet another embodiment of the present invention.
Figure 9:
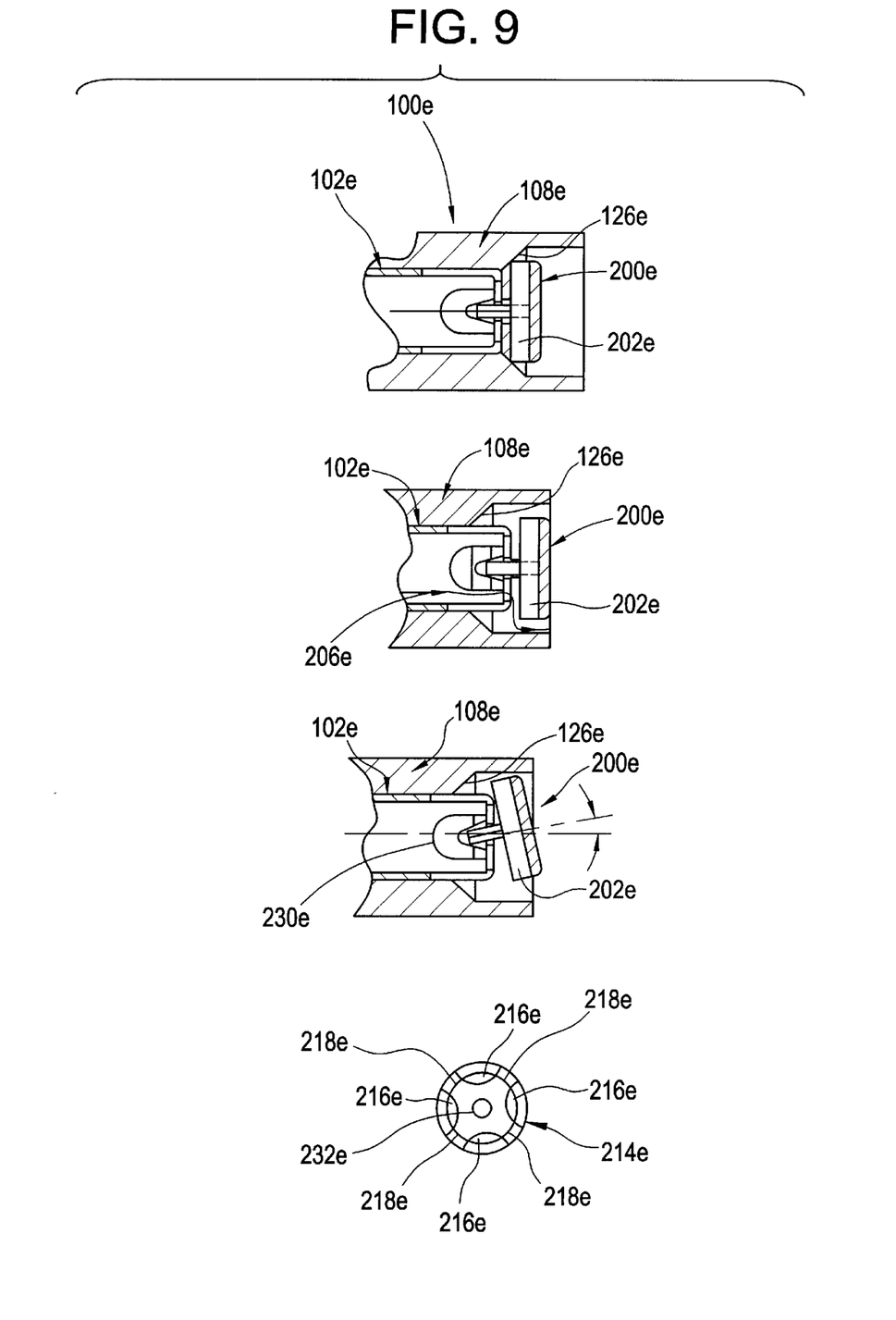
FIG. 9 is a set of views similar to FIGS. 7 and 8, but relating to a valve which is in accordance with still yet another embodiment of the present invention.

Several different valves are shown in FIGS. 3–9. A valve 100a which is in accordance with a first embodiment of the present invention is shown in FIGS. 3–5, a valve 100b which is in accordance with a second embodiment of the present invention is shown in FIG. 6, a valve 100c which is in accordance with a third embodiment of the present invention is shown in FIG. 7, a valve 100d which is in accordance with a fourth embodiment of the present invention is shown in FIG. 8, and a valve 100e which is in accordance with a fifth embodiment of the present invention is shown in FIG. 9.

Each of the valves shown in FIGS. 3–9 provides that fewer components are within the fluid flow path. As a result, each valve provides increased flow rate, a relatively unobstructed fluid flow path, and less turbulent fluid flow. Additionally, each valve minimizes the residual volume (i.e. "dead areas") contributing to fluid entrapment, and each provides enhanced backpressure tolerance when the valve is in the closed position. Additionally, the valves are inexpensive and easy to manufacture. Specifically, the valves shown in FIGS. 3–6 provide that assembly can be performed solely through one end of the valve body, as opposed to some components having to be installed through one end of the valve body and other components of the valve having to be installed through the other end of the valve body during the assembly process.

The valve 100a shown in FIGS. 3–5 will be described first and then the differences between the other valves 100b–100e and the valve 100a shown in FIGS. 3–5 will be described. The valve 100a shown in FIGS. 3–5 includes a valve core 102a, a pair of sealing members 104a, 106a which are disposed on the valve core 102a, a valve body 108a, and spring means 110a which is disposed in the valve body 108a, generally between the valve core 102a and the valve body 108a. The valve core 102a and valve body 108a are preferably made of plastic, while the sealing members 104a, 106a are preferably made of rubber or silicone, and the spring means 110a is preferably made of metal.

As shown, the valve body 108a is a generally hollow, cylindrical component having a central throughbore 112a. The valve body 108a may be made of, for example, clear plastic. The valve body 108a has a distal end 114a as well as a proximal end 116a which is generally opposite the distal end 114a. As shown in FIG. 5, both the valve core 102a (including the sealing members 104a, 106a which are disposed thereon) and the spring means 110a are installed through the distal end 114a of the valve body 108a to assemble the valve 100a.

The distal end 114a of the valve body is preferably configured for a male luer fitting. Specifically, the valve body 108a preferably includes threading 118a at the distal end 114a for engagement with corresponding mating structure 120 (see FIG. 4), such as a syringe, another valve, or some other structure, in a luer lock arrangement.

The valve body 108a includes a main body wall 122a which effectively defines the external surface of the valve 100a, and internal walls 124a which are connected to the main body wall 122a. As will be described more fully later herein, the internal walls 124a define sealing surfaces 126a which cooperate with ports 130a on the valve core 102a to prevent fluid flow through the valve 100a.

The internal walls 124a of the valve body 108a and the main body wall 122a of the valve body 108a define a pocket 132a, and the spring means 110a is disposed in the pocket 132a. Specifically, the spring means 110a is preferably a metal compression spring which has one end disposed in the pocket 132a in the valve body 108a and has an opposite end contactably engaged with a shoulder 134a on the valve core 102a. The end 135a of the valve core 102a preferably includes barbs 136a, or some other suitable structure, for generally retaining the valve core 102a in the valve body 108a, and preventing the valve core 102a from being pushed completely out of the valve body 108a by the compression spring 110a (via contactable engagement with internal surface 138a of the valve body 108a—see FIG. 3). Additionally, the barbs 136a provide that the valve core 102a can be snapped into the valve body 108a through the distal end 114a during assembly (see FIG. 5).

The valve core 102a is a generally hollow, cylindrical member having a central throughbore 140a. The central throughbore 140a extends along a longitudinal axis 142a of the valve core 102a and defines a fluid flow area. The valve core 102a includes a forward portion 144a, middle portion 146a which provides shoulder 134a, and a rearward portion 148a. Consistent with the configuration of the distal end 114a of the valve body 108a, the forward portion 144a of the valve core 102a preferably has a male luer taper to facilitate the luer lock engagement with the corresponding mating structure. Specifically, preferably the forward portion 144a of the valve core 102a has a standard ANSI/ISO luer configuration. The middle portion 146a of the valve core 102a (which provides shoulder 134a) contactably engages an internal surface 150a of the valve body 108a and is disposed between the forward (144a) and rearward (148a) portions of the valve core 102a. As shown in FIG. 4, when mating structure 120, such as a syringe, another valve, or some other structure is engaged with the valve 100a, the structure 120 pushably engages the middle portion 146a of the valve core 102a causing the valve core 102a to translate or slide relative to the valve body 108a which causes the compression spring 110a to compress and the valve 100a to actuate into the open position as shown in FIG. 4.

As shown in FIGS. 3–5, the valve core 102a includes a pair of ports 130a on the rearward portion 148a of the valve core 102a. The ports 130a are effectively openings through the surface of the valve core 102a, in communication with the central throughbore 140a (and the fluid flow area defined thereby). Preferably, the ports 130a on the valve core 102a are 180 degrees apart relative to each other along the external circumferential surface of the rearward portion 148a of the valve core 102a.

The valve 100a shown in FIGS. 3–5 provides that there are a pair of sealing members 104a, 106a disposed on the valve core 102a proximate the ports 130a on the valve core 102a. The sealing members 104a, 106a may comprise o-rings. Specifically, one sealing member 104a is disposed on the valve core 102a between the ports 130a and the middle portion 146a of the valve core 102a, and another sealing member 106a is disposed on the valve core 102a between the ports 130a and the end 135a of the valve core 102a. As shown in FIG. 5, glands 151a are preferably provided on the external surface of the valve core 102a for seating the sealing members 104a, 106a on the valve core 102a.

The valve 100a is configured such that the one sealing member 104a always remains engaged with the sealing surfaces 126a in the valve 100a which are provided by the internal walls 124a of the valve body 108a regardless of whether the valve 100a is in the closed (see FIG. 3) or open (see FIG. 4) position. Sealing member 104a prevents fluid from leaking into the area in which the spring 110a is located, and does so regardless of whether the valve 100a is in the closed (see FIG. 3) or open (see FIG. 4) position. The valve 100a is configured such that the other sealing member 106a is engaged with the sealing surfaces 126a when the valve 100a is in the closed position (see FIG. 3), but becomes disengaged therefrom when the valve 100a is actuated into the open position (see FIG. 4). Hence, the sealing member 106a prevents fluid communication between the valve ports 130a and a fluid flow area 152a of the valve body 108a when the valve 100a is in the closed (see FIG. 3) position.

Additionally, the valve 100a is configured such that the ports 130a on the valve core 102a align with the sealing surfaces 126a in the valve 100a when the valve 100a is in the closed position (see FIG. 3), but move out of alignment with the sealing surfaces 126a when the valve 100a is actuated into the open position (see FIG. 4).

The valve body 108a includes internal slots 154a which correspond with the ports 130a in the valve core 102a, and fluid flow area 152a of the valve body 108a is adjacent the slots 154a. Preferably, each of the slots 154a in the valve body 108a is larger than each of the respective ports 130a of the valve core 102a, and each of the ports 130a of the valve core 102a is larger than a cross-sectional diameter 156a of the central throughbore 140a which extends through the valve core 102a. This limits the fluid flow only to that permitted by the inside diameter 156a of the standard ANSI/ISO luer configuration, which comprises the distal end 114a of the valve core 102a.

The valve core 102a also includes a seal surface 160a on its rearward portion 148a which effectively seals off the slots 154a on the valve body 108a when the valve 100a is in the closed position as shown in FIG. 3. However, when the valve 100a is actuated into the open position (see FIG. 4), the ports 130a of the valve core 102a move out of alignment with the sealing surfaces 126a of the valve 100a and into alignment with the corresponding slots 154a in the valve body 108a, thereby defining a fluid flow path through the valve 100a (one possible fluid flow direction is represented by arrows 162a shown in FIG. 4). Specifically, in a direction from left-to-right in FIG. 4, the fluid flow path is: into the throughbore 140a in the valve core 102a, through the ports 130a in the valve core 102a, through the corresponding slots 154a in the valve body 108a, into the fluid flow area 152a of the valve body 108a and out the end 162a of the valve 100a. In the other direction, i.e. in a direction from right-to-left in FIG. 4, the fluid flow path is: into the end 162a of the valve 100a, through the slots 154a in the valve body 108a, through the ports 130a in the valve core 102a, and along (and out) the throughbore 140a in the valve core 102a.

Before mating structure 120, such as a syringe, another valve, or some other structure is engaged with the valve 100a, the valve 100a is in the closed position as shown in FIG. 3. In the closed position, the valve core 102a is biased into the closed position by the spring means 110a, the ports 130a in the valve core 102a are aligned with the sealing surfaces 126a in the valve body 108a, and both sealing members 104a, 106a on the valve core 102a sealingly engage the sealing surfaces 126a, thereby preventing fluid flow between the central throughbore 140a in the valve core 102a and the fluid flow area 152a in the valve body 108a. When mating structure 120 engages the valve 100a, the mating structure 120 pushes the valve core 102a into the valve body 108a, causing the valve 100a to be actuated into the open position as shown in FIG. 4. In the open position, the spring 110a is compressed, the ports 130a in the valve core 102a are aligned with the corresponding slots 154a in the valve body 108a, and only sealing member 104a on the valve core 102a remains sealingly engaged with the sealing surfaces 126a. Hence, fluid flow is permitted between the central throughbore 140a in the valve core 102a and the fluid flow area 152a in the valve body 108a.

The valve 100b shown in FIG. 6 is very similar to that shown in FIGS. 3–5, and includes a valve core 102b, a valve body 108b and a spring means 110b very much like the valve 100a shown in FIGS. 3–5. However, instead of providing that two sealing members, such as o-rings, are disposed on the valve core, the valve 100b shown in FIG. 6 provides that a sealing material 104b is co-injected or over-molded onto the exterior surface of the valve core 102b, on the forward 144b and rearward 148b portions. Functionally, the sealing material 104b which is on the rearward portion 148b of the valve core 100b performs the same function as the sealing members 104a, 106a shown in FIGS. 3–5. The sealing material 104b which is on the forward portion 144b of the valve core 102b works to provide a seal between the mating structure 120 and the valve core 102b. The sealing material 104b which is co-injected or over-molded onto the exterior surface of the valve core 102b may consist of a rigid substrate material with a different resilient outer surface material shell. The employment of co-injection or over-molding for the valve core 104b eliminates the requirement of o-ring seals in the design (see FIGS. 3–5) and further reduces the component part count.

The valves 100c, 100d, 100e shown in FIGS. 7–9 are similar to that shown in FIGS. 3–6, and each includes a valve core 102c, 102d, 102e, valve body 108c, 108d, 108e and spring means 110c, 110d (valve 100e also includes spring means much like the other valves 100a–100d, but the spring means is not specifically shown). However, unlike the valves 100a, 100b shown in FIGS. 3–6, each of the valves 100c, 100d, 100e shown in FIGS. 7–9 includes a self-aligning valve seat carrier 200c, 200d, 200e which is pivotably engaged (see the bottom-most cross-sectional view of FIGS. 7–9) with the valve core 102c, 102d, 102e. The valve body 108c, 108d, 108e of each of the valves 100c, 100d, 100e includes a sealing surface 126c, 126d, 126e which, as shown in FIGS. 7–9, may consist of an inclined surface which is inside the valve body 108c, 108d, 108e. The self-aligning valve seat carrier 200c, 200d, 200e also includes a sealing surface 202c, 202d, 202e provided by, for example, a sealing member which is disposed thereon.

The spring means 110c, 110d of each valve is engaged with the valve body 108c, 108d, 108e and the valve core 102c, 102d, 102e, and the spring means 110c, 110d biases the valve core 102c, 102d, 102e into a closed position (see the top-most cross-sectional view of each of FIGS. 7–9) wherein the sealing surface 202c, 202d, 202e of the self-aligning valve seat carrier 200c, 200d, 200e engages the sealing surface 126c, 126d, 126e of the valve body 108c, 108d, 108e, thereby prohibiting fluid flow through the valve 100c, 100d, 100e.

When mating structure 120 engages the valve core 102c, 102d, 102e, the valve core 102c, 102d, 102e slides within the valve body 108c, 108d, 108e such that the valve 100c, 100d, 100e is actuated to an open position (see the middle cross-sectional view of each of FIGS. 7–9) wherein the sealing surface 202c, 202d, 202e on the self-aligning valve seat carrier 200c, 200d, 200e disengages from the sealing surface 126c, 126d, 126e of the valve body 108c, 108d, 108e thereby allowing fluid flow through the valve 100c, 100d, 100e (as represented by arrows 206c, 206d, 206e). In the valve 100c shown in FIG. 7, the self-aligning valve seat carrier 200c preferably includes a hollow portion 210c that terminates in one or more openings 212c that allows fluid to flow through the valve seat carrier 200c. In the other valves 100d, 100e, the bottom 214d, 214e of the valve core 102d, 102e provides openings 216d, 216e which allow fluid flow between fingers 218d, 218e.

The self-aligning valve seat carrier may take several different configurations. For example, in the valve 100c shown in FIG. 7, the self-aligning valve seat carrier 200c includes a pair of arms 220c which engage corresponding recessed grooves 222c proximate the bottom 214c of the valve core 102c. The sealing member 202c which is disposed on the valve seat carrier 200c may consist of an o-ring. Alternatively, a sealing material may be co-injected or over-molded onto the exterior surface of the valve seat carrier.

In the valve 100d shown in FIG. 8, the self-aligning valve seat carrier 200d includes a ball 230d which engages a corresponding socket 232d on the valve core 102d, wherein the socket 232d is provided via the four fingers 218d which are at the bottom 214d of the valve core 102d (see the bottom-most view of FIG. 8). In the valve shown in FIG. 9, the self-aligning valve seat carrier 200e includes a barb 230e which engages corresponding structure 232e on the end 214e of the valve core 102e, wherein the corresponding structure 232e is provided via the four fingers 218e which are at the bottom 214e of the valve core 102e (see the bottom-most view of FIG. 9). The sealing member 202d, 202e which is disposed on each of the valve seat carriers 200d, 200e shown in FIGS. 8 and 9 may consist of an attached resilient seal material, wherein an additional seal is preferably provided at the valve carrier 200d, 200e valve body 108d, 108d interface. Alternatively, a sealing material may be co-injected or over-molded onto the exterior surface of the valve seat carrier 200d, 200e in each of the valves 100d, 100e shown in FIGS. 8 and 9.

Regardless, the fact that each valve seat carrier 200c, 200d, 200e is pivotable and self-aligning provides that each valve seat carrier 200c, 200d, 200e can articulate (as shown in the bottom-most cross-sectional view of each of FIGS. 7–9), and an enhanced seal is achieved between the sealing surface 126c, 126d, 126e of the valve body 108c, 108d, 108e and the valve seat carrier 200c, 200d, 200e when the valve 100c, 100d, 100e is in the closed position (the top-most cross-sectional view of each of FIGS. 7–9).

The bottom 214c, 214d, 214e of each of the valve cores 102c, 102d, 102e is shown in the bottom view of each of FIGS. 7–9. As shown, each of the valve cores 102d, 102e of valves 100d, 100e includes fingers 218d, 218e which engage the valve seat carrier 200d, 200e. With regard to the arrangement shown in FIG. 8, wherein the valve seat carrier 200d includes a ball 230d which is received in a corresponding socket 232d in the end 214d of the valve core 102d, in the closed position (the top view of FIG. 8), the fingers 218d of the valve core 102d are prevented from outward deflection by the valve body 108d. This prevents pressure exerted by the compression spring 100d from disengaging the ball 232d of the valve seat carrier 200d and allows the valve core 102d to escape from the assembly. In the open position (the middle view of FIG. 8), the fingers 218d of the valve core 102d are free to deflect outward by the ball 232d sufficiently to allow the ball 232d of the valve seat carrier 200d to be snapped into location and allow the valve seat carrier 200d to pivot, i.e. have angular movement.

Each of the valves 100a–100e shown in FIGS. 3–9 provides that fewer components are within the fluid flow path, that flow rate is increased (when the valve is open), that there is a relatively unobstructed fluid flow path, and that there is less turbulence introduced into the flow. Additionally, each valve minimizes dead areas which can contribute to fluid entrapment, and each provides enhanced backpressure tolerance when the valve is in the closed position. Additionally, the valves are inexpensive and easy to manufacture.

Specifically, valves 100a and 100b provide that assembly can be performed solely through one end (i.e. end 114a shown in FIG. 5) of the valve body 108a, 108b, as opposed to some components having to be installed through one end of the valve body and other components of the valve having to be installed through the other end of the valve body during the assembly process.

While embodiments of the present invention are shown and described, it is envisioned that those skilled in the art may devise various modifications of the present invention without departing from the spirit and scope of the foregoing disclosure.

What is claimed is:

1. A valve comprising: a valve body which includes a sealing surface and at least one internal slot; a valve core disposed in said valve body and including at least one port; spring means engaged with said valve body and said valve core, said spring means biasing said valve core into a closed position wherein said port of said valve core is aligned with said sealing surface of said valve body thereby prohibiting fluid flow through said valve, said valve core being slidable generally within said valve body to an open position wherein said port of said valve core is aligned with said internal slot of said valve body thereby allowing fluid flow through said valve.

2. A valve as defined in claim 1, wherein said valve core includes a body and a bore through said body along a longitudinal axis of said body, wherein said body of said valve core includes a wall and said port comprises an opening in said wall.

3. A valve as defined in claim 2, wherein said valve body includes a fluid flow area and the bore through said body of said valve core defines a fluid flow area, wherein a fluid flow path through said valve is defined by said fluid flow area defined by said bore through said body of said valve core and said fluid flow area of said valve body, and said spring means is not within said fluid flow path through said valve.

4. A valve as defined in claim 2, wherein said slot in said valve body is larger than said port of said valve core, and said port of said valve core is larger than a cross-sectional diameter of said bore through said valve core.

5. A valve as defined in claim 1, wherein said valve core includes two ports and said valve body includes two slots, said valve core being slidable generally within said valve body to an open position wherein said ports of said valve core are aligned with said slots of said valve body thereby allowing fluid flow through said valve.

6. A valve as defined in claim 5, wherein said ports of said valve core are 180 degrees apart and said slots of said valve body are 180 degrees apart.

7. A valve as defined in claim 1, wherein said slot in said valve body is larger than said port of said valve core.

8. A valve as defined in claim 1, wherein at least one end of said valve is configured for a Luer lock fitting.

9. A valve as defined in claim 1, further comprising at least one sealing member disposed on said valve core and engaged with said sealing surface of said valve body.

10. A valve as defined in claim 1, further comprising a first sealing member disposed on said valve core, said first sealing member engaged with said sealing surface of said valve body when said valve core is in said open and closed positions, and further comprising a second sealing member disposed on said valve core, said second sealing member engaged with said sealing surface of said valve body when said valve core is in said closed position, but disengaged from said sealing surface of said valve body when said valve core is in said open position.

11. A valve as defined in claim 1, said valve core including at least one barb which abuts against an internal surface of said valve body when said valve core is biased into said closed position by said spring means.

12. A valve as defined in claim 1, wherein said valve body includes a pocket and said valve core includes a shoulder, wherein said spring means is disposed in said pocket of said valve body and engages said shoulder of said valve core.

13. A valve as defined in claim 1, further comprising a resilient material at least one of over-molded and co-injected on said valve core.

14. A valve as defined in claim 13, wherein said resilient material is disposed on said valve core proximate said port.

* * * * *